US010765225B2

(12) United States Patent
O'Keefe et al.

(10) Patent No.: US 10,765,225 B2
(45) Date of Patent: Sep. 8, 2020

(54) OCCUPANT SUPPORT WITH A MIGRATION SENSITIVE BLADDER AND METHOD FOR MIGRATION DETECTION

(71) Applicant: Hill-Rom Services, Inc., Batesville, IN (US)

(72) Inventors: Christopher R. O'Keefe, Columbus, OH (US); Timothy J. Receveur, Guilford, IN (US); Aziz A. Bhai, Fishers, IN (US); Luke Gibson, Greensburg, IN (US); Charles A. Lachenbruch, Batesville, IN (US); Rachel Williamson, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 614 days.

(21) Appl. No.: 15/597,784

(22) Filed: May 17, 2017

(65) Prior Publication Data

US 2017/0246062 A1    Aug. 31, 2017

Related U.S. Application Data

(63) Continuation of application No. 13/443,234, filed on Apr. 10, 2012, now Pat. No. 9,655,795.

(51) Int. Cl.
*A47C 27/08* (2006.01)
*A47C 27/10* (2006.01)
*A61G 7/057* (2006.01)

(52) U.S. Cl.
CPC ............ *A47C 27/083* (2013.01); *A47C 27/10* (2013.01); *A47C 27/08* (2013.01); *A61G 7/05769* (2013.01)

(58) Field of Classification Search
CPC ..... A47C 27/08; A47C 27/081; A47C 27/083; A47C 27/10; A61G 7/05769;
(Continued)

(56) References Cited

U.S. PATENT DOCUMENTS 5,092,415 A    3/1992 Asano
5,170,364 A    12/1992 Gross et al.
(Continued)

FOREIGN PATENT DOCUMENTS

EP    1093755 A1    4/2001
EP    2301429 A1    3/2011
(Continued)

OTHER PUBLICATIONS

EP Official Letter in Application No. 13 162 972.7-1657, dated Mar. 17, 2017.
(Continued)

*Primary Examiner* — Robert G Santos
(74) *Attorney, Agent, or Firm* — Barnes & Thornburg LLP

(57) ABSTRACT

A method for detecting occupant position change on a support surface includes establishing a rate of change of pressure in a head end test zone and in a foot end test zone, comparing the head end rate to at least one head end rate limit, comparing the foot end rate to at least one foot end rate limit, and inferring, in response to the comparing steps, whether or not occupant migration has occurred. An associated occupant support includes a frame and a mattress. The mattress includes head and foot zones each having at least one pressurizable bladder. The support also includes a controller adapted to compare a head end rate of pressure change to a head end rate limit, to compare a foot end rate of pressure change to a foot end rate limit, and to infer, in response to the comparing steps, whether or not occupant migration has occurred.

20 Claims, 13 Drawing Sheets

(58) Field of Classification Search
CPC .... A61G 7/05776; G08B 21/02; G08B 21/06; G08B 21/18; G08B 21/182; G08B 21/22
USPC ............... 5/713, 710, 706, 655.3, 654, 644; 340/573.1
See application file for complete search history.

(56) References Cited

U.S. PATENT DOCUMENTS

| | | | |
|---|---|---|---|
| 6,719,708 B1 | 4/2004 | Jansen | |
| 8,090,478 B2 | 1/2012 | Skinner et al. | |
| 8,533,879 B1 | 9/2013 | Taylor | |
| 8,620,477 B2* | 12/2013 | Skinner | A61G 7/05769 700/281 |
| 8,875,331 B2 | 11/2014 | Taylor | |
| 9,107,511 B2* | 8/2015 | Skinner | A61G 7/05769 |
| 9,329,076 B2* | 5/2016 | Meyer | A61G 7/002 |
| 9,510,688 B2* | 12/2016 | Nunn | A61B 5/01 |
| 9,635,953 B2* | 5/2017 | Nunn | A47C 27/083 |
| 9,655,457 B2* | 5/2017 | Meyer | A61G 7/053 |
| 9,655,795 B2 | 5/2017 | O'Keefe et al. | |
| 9,833,369 B2* | 12/2017 | Meyer | A61G 7/018 |
| 9,844,275 B2* | 12/2017 | Nunn | A47C 21/003 |
| 10,251,490 B2* | 4/2019 | Nunn | A47C 27/083 |
| 10,441,086 B2* | 10/2019 | Nunn | A47C 27/083 |
| 10,485,355 B2* | 11/2019 | Yu | A47C 27/084 |
| 10,492,619 B2* | 12/2019 | Ohno | A47C 27/10 |
| 10,555,850 B2* | 2/2020 | Meyer | A61G 7/008 |
| 2008/0189865 A1 | 8/2008 | Bhai | |
| 2010/0063638 A1 | 3/2010 | Skinner | |
| 2011/0144455 A1 | 6/2011 | Young et al. | |
| 2012/0054964 A1 | 3/2012 | Stroh et al. | |
| 2012/0174322 A1* | 7/2012 | Skinner | A47C 27/08 5/713 |
| 2013/0263378 A1 | 10/2013 | O'Keefe et al. | |
| 2013/0340168 A1* | 12/2013 | Meyer | A61G 7/0506 5/615 |
| 2014/0102567 A1* | 4/2014 | Skinner | A47C 27/08 137/624.11 |
| 2014/0123390 A1* | 5/2014 | Meyer | G01G 19/445 5/615 |
| 2014/0259418 A1* | 9/2014 | Nunn | A47C 21/003 5/617 |
| 2014/0259434 A1* | 9/2014 | Nunn | A47C 27/083 5/713 |
| 2014/0277778 A1* | 9/2014 | Nunn | A47C 31/00 700/282 |
| 2014/0026327 A1 | 11/2014 | Taylor | |
| 2015/0182400 A1* | 7/2015 | Meyer | A61G 7/05776 5/710 |
| 2017/0049243 A1* | 2/2017 | Nunn | A61B 5/6892 |
| 2017/0086598 A1* | 3/2017 | Ohno | G05D 7/0676 |
| 2017/0196369 A1* | 7/2017 | Nunn | G05B 19/0428 |
| 2017/0224560 A1* | 8/2017 | Meyer | A61G 7/001 |
| 2017/0246062 A1* | 8/2017 | O'Keefe | A61B 5/1036 |
| 2018/0064593 A1* | 3/2018 | Meyer | A61G 7/0509 |
| 2019/0021513 A1* | 1/2019 | Nunn | A47C 27/083 |
| 2019/0075931 A1* | 3/2019 | Yu | A47C 27/10 |
| 2019/0174931 A1* | 6/2019 | Ohno | A47C 31/123 |
| 2019/0231084 A1* | 8/2019 | Nunn | A47C 27/10 |
| 2019/0328147 A1* | 10/2019 | Palashewski | A61B 5/1118 |
| 2020/0054149 A1* | 2/2020 | Ohno | G05B 15/02 |

FOREIGN PATENT DOCUMENTS

| | | |
|---|---|---|
| GB | 2320759 A | 7/1998 |
| GB | 2453371 A | 4/2009 |
| WO | 2006135845 A2 | 12/2006 |
| WO | 2007016054 A2 | 2/2007 |
| WO | 2009120270 A2 | 10/2009 |
| WO | 2011113070 A1 | 9/2011 |

OTHER PUBLICATIONS

EP Search Report for EP Application 13162972.7—dated Aug. 20, 2013; Place of Search—The Hague; Date of Completion of the Search—Aug. 6, 2013.

* cited by examiner

|  Least Recent Value | | Most Recent Value |
| --- | --- | --- |
| $t_{-2}$ | $t_{-1}$ | $t_0$ |
| $P_{-2}$ | $P_{-1}$ | $P_0$ |

| ZONE | BLADDER | TEST | BLADDER SPECIFIC TEST RESULT | ZONE TEST RESULT | OVERALL RESULT |
|------|---------|------|------------------------------|------------------|----------------|
| HEAD | H1<br>H2<br>H3<br>H4 | CYCLE COUNT<br>CYCLE COUNT<br>CYCLE COUNT<br>CYCLE COUNT | F<br>T<br>F<br>F | T | |
| HEAD | H1<br>H2<br>H3<br>H4 | ΔP EXCEEDANCE<br>ΔP EXCEEDANCE<br>ΔP EXCEEDANCE<br>ΔP EXCEEDANCE | F<br>F<br>F<br>T | T | T |
| FOOT | F1<br>F2<br>F3<br>F4 | CYCLE COUNT<br>CYCLE COUNT<br>CYCLE COUNT<br>CYCLE COUNT | F<br>F<br>T<br>F | T | |
| FOOT | F1<br>F2<br>F3<br>F4 | ΔP EXCEEDANCE<br>ΔP EXCEEDANCE<br>ΔP EXCEEDANCE<br>ΔP EXCEEDANCE | T<br>F<br>F<br>F | T | |

FIG. 15

OCCUPANT SUPPORT WITH A MIGRATION SENSITIVE BLADDER AND METHOD FOR MIGRATION DETECTION

PRIORITY CLAIM

This application is a continuation of U.S. application Ser. No. 13/443,234, filed Apr. 10, 2012, which will issue May 23, 2017 as U.S. Pat. No. 9,655,795 and which is expressly incorporated by reference herein.

TECHNICAL FIELD

The subject matter described herein relates to an apparatus and method for detecting a position or a change in position of an occupant of an occupant support, such as a hospital bed.

BACKGROUND

Patients in hospitals, other health care facilities and home care settings may be confined to a bed for an extended period of time. Such beds may include articulable components so that the occupant or a caregiver can adjust the profile of the bed. The beds may also include components for applying selected therapies to the occupant. The use of articulating and therapeutic features may cause the occupant to migrate from an optimum location or position on the bed to another location or position, usually closer to the foot end of the bed. Even if articulating and therapeutic features are unavailable or unused, the occupant can nevertheless migrate from the optimal location to a nonoptimal location. Occupant migration refers to, for example, an involuntary change in occupant position in at least the longitudinal direction, and is distinct from intentional movements such as an occupant voluntarily repositioning himself or being repositioned by a caregiver. The migration, in addition to placing the occupant in a nonoptimal location, can also impose undesirable shear stresses on the occupant's skin. It is, therefore, desirable to monitor occupant location so that a caregiver or automated system can assess the need for a corrective or mitigating action.

SUMMARY

The present application describes a method for detecting occupant position change on a support surface. The method includes establishing a rate of change of pressure in a head end test zone and in a foot end test zone, comparing the head end rate to at least one head end rate limit, comparing the foot end rate to at least one foot end rate limit, and inferring, in response to the comparing steps, whether or not occupant migration has occurred. An associated occupant support includes a frame and a mattress. The mattress includes head and foot zones each having at least one pressurizable bladder. The support also includes a controller adapted to compare a head end rate of pressure change to a head end rate limit, to compare a foot end rate of pressure change to a foot end rate limit, and to infer, in response to the comparing steps, whether or not occupant migration has occurred.

BRIEF DESCRIPTION OF THE DRAWINGS

The subject matter described herein relates to an apparatus and method for detecting a position or a change in position of an occupant of an occupant support, such as a hospital bed. The foregoing and other features of the various embodiments of the occupant support and method described herein will become more apparent from the following detailed description and the accompanying drawings in which:

FIG. 15 is a table showing an example of application of the method of FIGS. 12-14 to a bed having multiple bladders in the head and foot zones.

DETAILED DESCRIPTION

Figure 1:
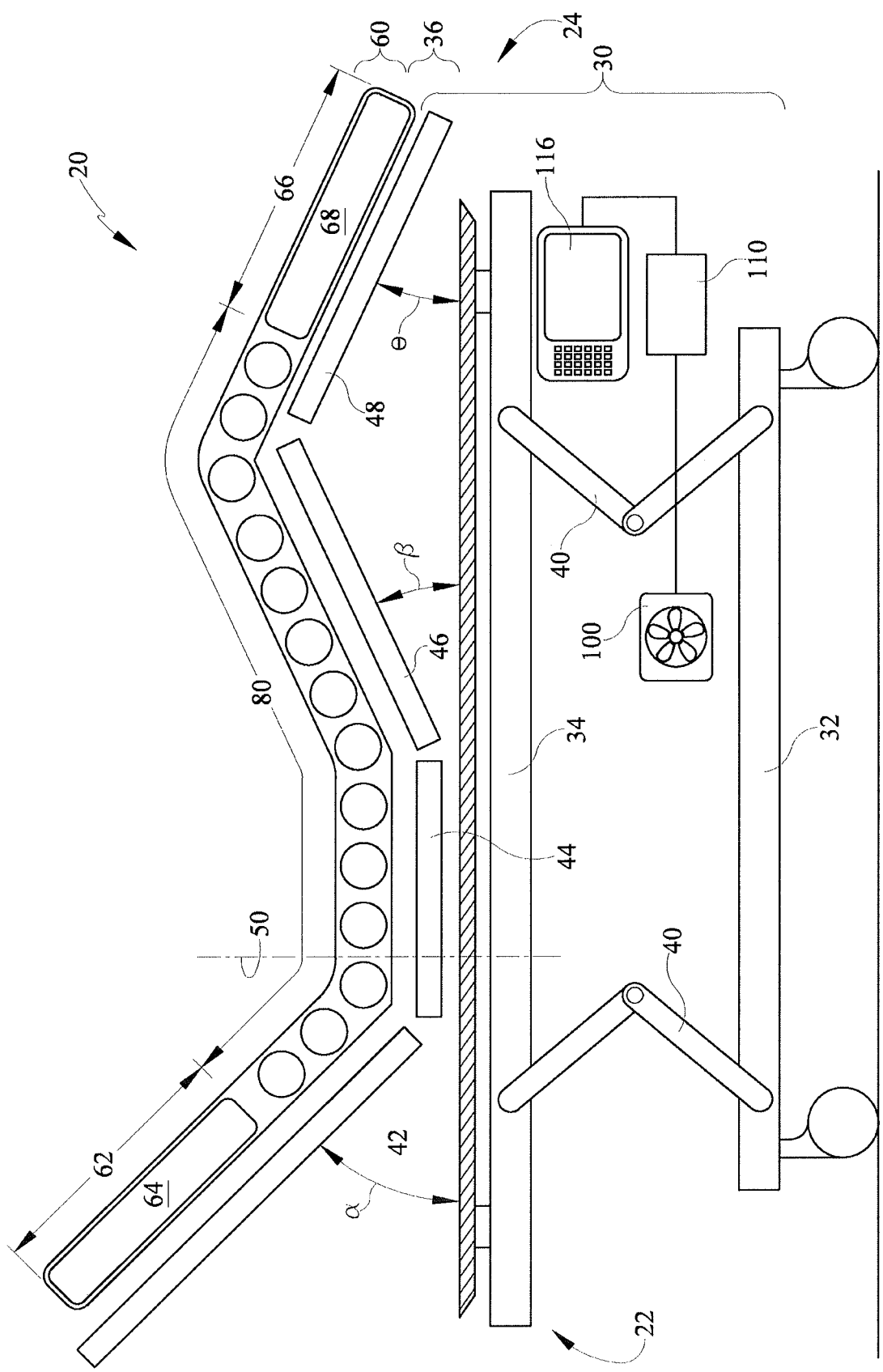
FIG. 1 is a schematic side elevation view of a hospital bed having a frame and a mattress in which the mattress is comprised of a head end bladder in a head zone, a foot end bladder in a foot zone and a series of intermediate bladders in an intermediate zone between the head and foot zones.

FIG. 1 illustrates a bed 20 which extends longitudinally from a head end 22 to a foot end 24 and laterally from a right side, visible in the illustration, to a left side. The bed comprises a frame 30 which includes a base frame 32, an elevatable frame 34, and a deck 36. A lift system, represented by links 40 in the illustration, connects the elevatable frame to the base frame so that the elevation of the elevatable frame can be adjusted. Deck 36 comprises an upper body or torso section 42, a seat section 44, a thigh section 46 and a calf section 48 corresponding approximately to an occupant's torso, buttocks, thighs and calves respectively. The angular orientations of the torso, thigh and calf sections are adjustable as indicated by angles $\alpha$, $\beta$, and $\theta$ in the illustration. Siderails, not illustrated, border the left and right sides of the bed and include a hip indicator which corresponds to hip plane 50 in the illustration. The hip indicator indicates the approximate longitudinal location at which the occupant's hip should be positioned so that the occupant is optimally located on the bed.

The bed also includes a mattress 60 supported by the frame. The mattress includes a head zone 62 having at least one fluid pressurizable bladder 64 and a foot zone 66 also having at least one fluid pressurizable bladder 68. It should be appreciated that the head zone and foot zone are so named because they are located at or near the head end and foot end extremities of the mattress; the zones do not necessarily correspond exactly to the location of an occupant's head or feet. For reasons that will become apparent the head and foot zones are also referred to herein as head and foot test zones and the bladders in those zones may be referred to as head and foot test bladders. The head zone and the foot zone are longitudinally separated from each other by an intermediate zone 80.

Figure 2:
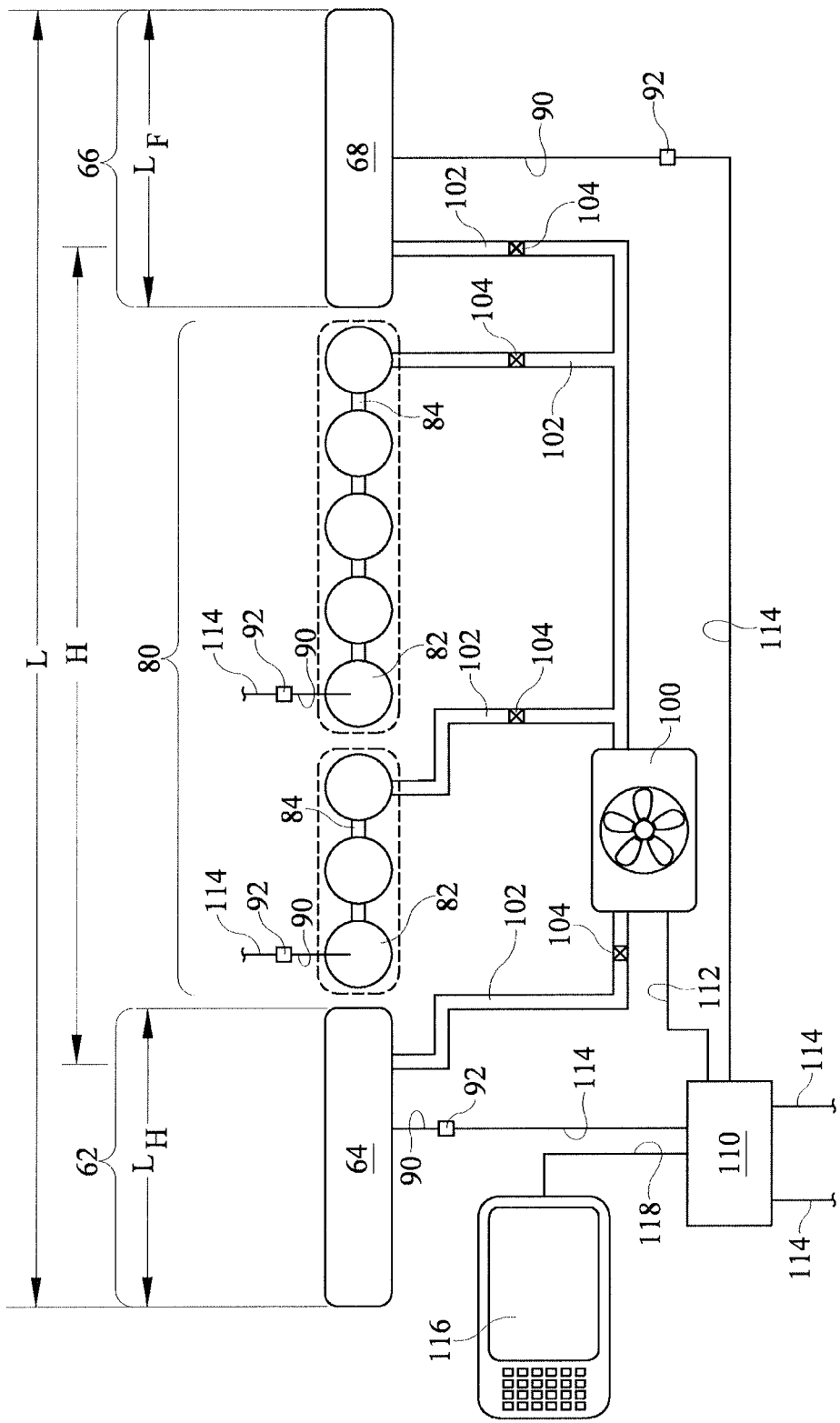
FIG. 2 is a schematic side elevation view showing a mattress similar to that of FIG. 1 and also showing fluid and communication lines extending between the bladders and other components.
Figure 3:
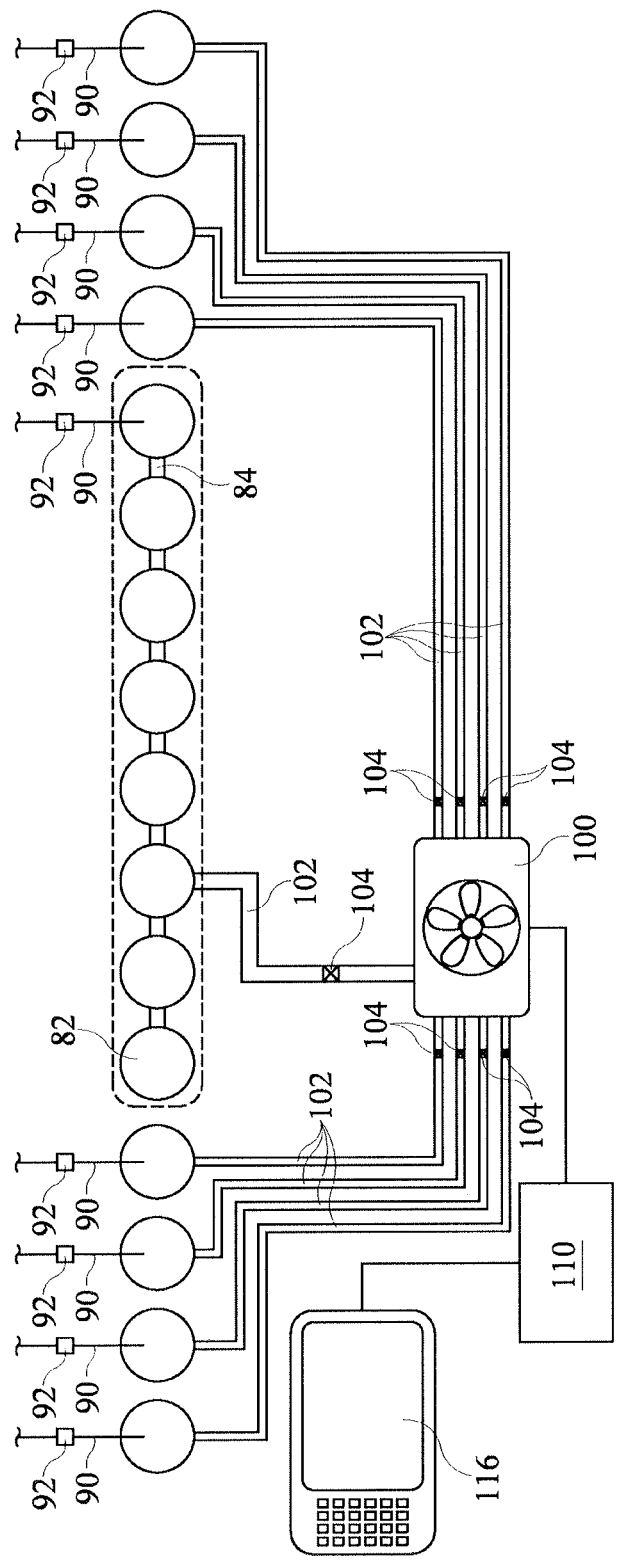
FIG. 3 is a view similar to FIG. 2 but having multiple bladders in the head and foot zones.

FIGS. 2-6 show a selection of mattress architectures. FIGS. 2 and 3, like FIG. 1, show a mattress in which the intermediate zone 80 comprises a series of longitudinally distributed pressurizable bladders 82 which are the principal medium or structure for supporting an occupant of the mattress (i.e. an occupant of the bed) in the intermediate zone. However a structure other than bladders, for example a foam, could be used in the intermediate zone in which case the alternative medium will be the principal medium or structure for supporting an occupant in the intermediate zone. The intermediate bladders may be grouped together in one or more groups with bladders of a given group connected to their neighboring bladders in the same group buy a fluid passage 84. The intermediate zone of FIG. 2 includes two groups of bladders, a first group comprising three bladders and a second group comprising five bladders. The intermediate zone of FIG. 3 includes a single group. A pressure sense tube 90 extends from the head bladder (or from each of multiple head bladders) from the foot bladder (or from each of multiple foot bladders) and from one bladder in each group of intermediate bladders to a pressure transducer 92 dedicated to each bladder or group. In bed architectures that employ multiple head and/or foot bladders, such as the architecture of FIG. 3, the bladders in the head zone are pneumatically isolated from each other and the bladders in the foot zone are pneumatically isolated from each other and each of the bladders has a sense line 90 and a pressure transducer 92.

Figures 4, 5, 6:
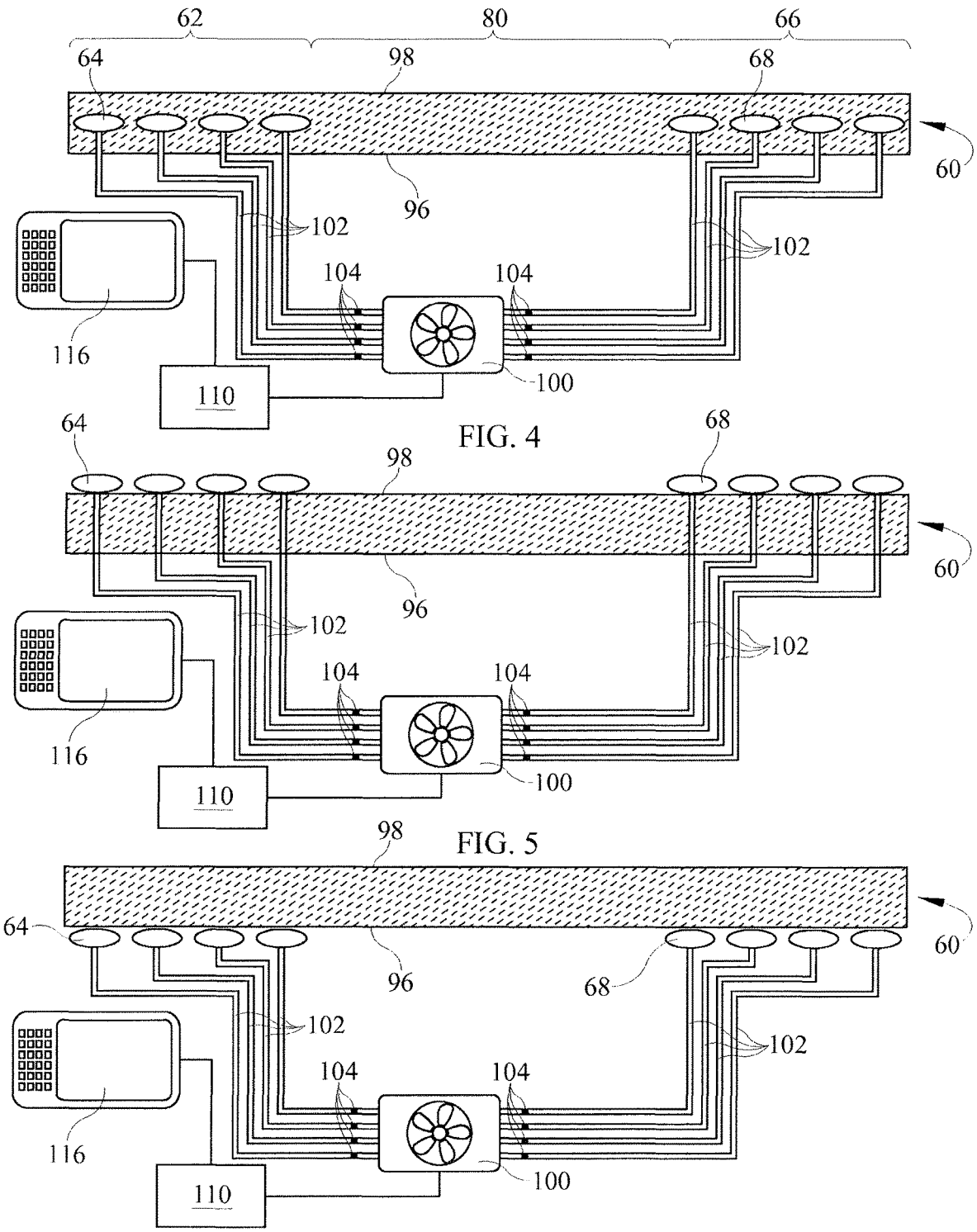
FIGS. 4-6 are views similar to FIGS. 2-3 in which the intermediate zone is a foam material that extends into the head and foot zones and in which bladders also occupy the head and foot zones.

FIGS. 4-6 show variations of a third architecture in which a component other than bladders, such as foam, comprises the principal supporting structure of the mattress in the intermediate zone and in which the foam medium extends into the head zone, the foot zone or both (as illustrated) for at least partially supporting the occupant. The foam medium has a frame side 96 and an occupant side 98. The head zone and foot zone each contain at least one bladder. The head zone bladder or bladders may be embedded in the foam medium (FIG. 4) exposed on the occupant side of the medium (FIG. 5) or exposed on the frame side of the medium (FIG. 6). The architecture of FIGS. 4-6 also include pressure sense lines and transducers as already described, however these components are not shown in FIGS. 4-6.

A blower 100 is connected to selected bladders by a network of fluid supply tubes 102 and appropriate valves 104 for supplying fluid, typically ambient air, to the bladders. The blower is connected to each of the head and foot bladder or bladders 64, 68 and to each group of intermediate bladders 82 in architectures that employ intermediate bladders (FIGS. 2-3). The blower can be operated to pump air into the bladders thereby pressurizing them. The blower can also be operated to suction air out of the bladders thereby depressurizing them. Alternatively depressurization can be achieved by venting a bladder to atmosphere.

A controller 110 communicates with blower 100 by way of a communication link represented by line 112. Pressure readings from pressure transducers 92 are communicated to the controller by communication links represented by lines 114. A user interface 116 allows the bed occupant, a caregiver, or other user to communicate instructions to the controller by way of communication link represented by line 118.

In the above described beds the test bladders, i.e. the head and foot end bladders 64, 68, are a set of one or more bladders in the head zone near the head end of the bed and in the foot zone near the foot end of the bed and are separated from each other by a non-test or intermediate zone which may or may not comprise bladders. The quantity of test bladders depends on the degree of granularity considered to be acceptable to carry out the method described below. As seen in FIG. 2, the combined lengths LF, LH of the test zones is greater than mattress length L reduced by the height H of a minimum height occupant, for example a 5th percentile female, i.e.

$$LF+LH>L-H \qquad (1)$$

In the illustrations the lengths of the test zones are shown as equally apportioned between the head and foot ends of the bed, however unequal apportionment may suffice or even be advantageous.

Alternatively all the bladders on the bed could be employed as test bladders in which case inequality (1) no longer applies.

Controller 110 receives pressure readings from the transducers and operates the blower and valves to maintain bladder pressure in a range bounded by upper and lower limits so that bladder pressure remains approximately equal to a set point pressure. For example, if an occupant's weight shifts partly or completely off a bladder, the fluid pressure in the bladder can decrease to or below the lower limit. In response, the controller operates the blower and valves to increase the pressure to the set point pressure. Conversely, if additional occupant weight shifts onto a bladder, the bladder pressure can increase to or above the upper limit. In response, the controller operates the blower and valves to decrease the pressure to the set point pressure. Such regulation of bladder pressure helps ensure that the magnitude and distribution of the interface pressure imposed on the occupant by the mattress remains satisfactory.

Figure 7:
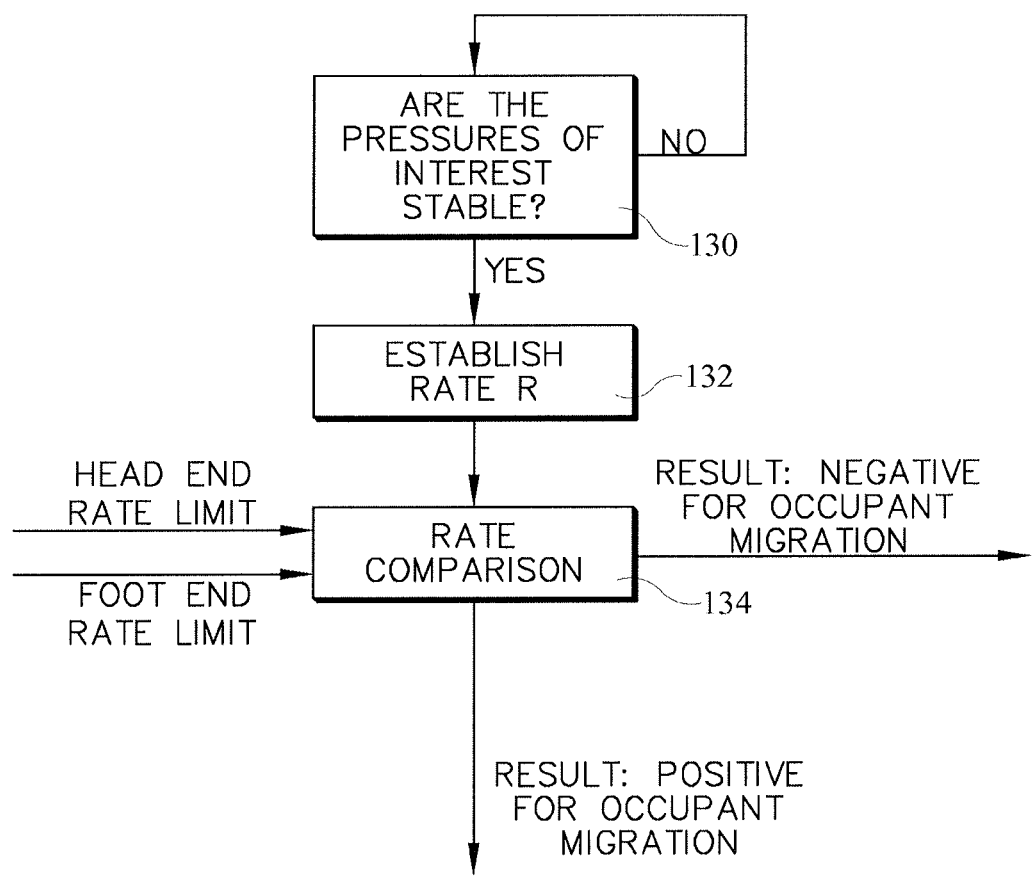
FIG. 7 is a block diagram showing a generic version of a method of detecting a change in occupant location on the mattresses of FIGS. 1-6.
Figures 8A, 8B:
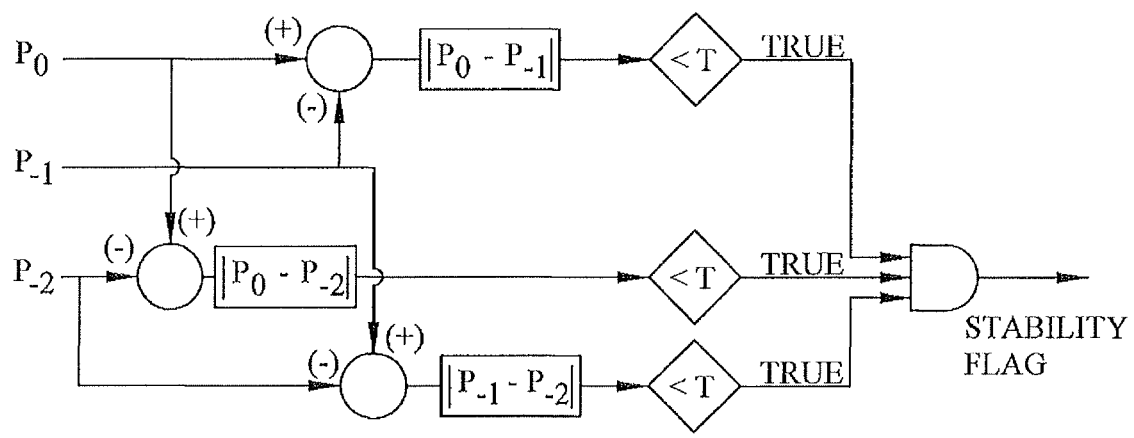
FIGS. 8A and 8B show a data queue and a diagram of a pressure stability test that uses the data from the data queue.

FIG. 7 shows a generic version of a method of detecting a change in occupant location on the mattress. In general, the method conducts a stability test on bladder pressures of interest at block 130. The stability test determines whether or not the pressures of interest are undergoing a transient, and is shown in more detail in FIGS. 8A-8B. The pressures of interest are the pressure in the head zone bladder or bladders 64 and the pressure in the foot zone bladder or bladders 68. The stability test is carried out because the method of detecting a change in occupant location relies on establishing the existence of a change in pressure per unit time and therefore requires information to ensure that the pressures are not changing just before the onset of the pressure change whose rate is to be determined and just after the conclusion of the pressure change whose rate is to be determined, particularly if the pressure change per unit time is based on a simple difference of two pressures at two different times. Other methods of determining the pressure change per unit time may not require a stability test. The example stability test maintains a queue of time values t0, t−1 and t−2 and a queue of pressure values $P_0$, $P_{-1}$ and $P_{-2}$ at each of those times (FIG. 8A). The queue is periodically updated by discarding the least recent time and pressure values and adding a new time and pressure value to the other end of the queue. The block diagram of FIG. 8B shows that a stability flag is set to TRUE (indicating that the pressures are stable) if the absolute values of all three pressure differences in the queue are less than a pressure difference threshold T.

Returning to FIG. 7, if the pressures of interest are stable, the method proceeds to block 132 where the controller establishes the rate of change of bladder pressure in the bladders of the head and foot zones. As discussed below in more detail, certain rates of pressure change may reveal that an occupant has migrated longitudinally along the bed, or at least allow an inference that migration has occurred. Determination of the rate of change of bladder pressure can be based on observing the time required to achieve a given change in pressure, or can be based on observing the pressure change achieved over a fixed time interval, or can be a calculated $\Delta p/\Delta t$ in which neither $\Delta p$ or $\Delta t$ are prescribed, or can be a more sophisticated determination of the time derivative $dp/dt$.

Regarding rates of change of pressure, an increase in pressure is considered to be a positive change in pressure so that the corresponding rate of change is also positive. Expressions of relative rates of pressure increase (e.g. the actual rate of pressure increase in comparison to a rate limit) are governed by the magnitude of the rate. For example a pressure increase whose rate is 6 pressure units per unit time is less than or slower than a pressure increase whose rate is 8 pressure units per unit time and greater than or faster than a pressure increase whose rate is 4 pressure units per unit time. A decrease in pressure is considered to be a negative change in pressure so that the corresponding rate of change is also negative. Expressions of relative rates of pressure decrease are governed by the absolute magnitude of the rate. For example a pressure decrease whose rate is 7 pressure units per unit time is less than or slower than a pressure increase whose rate is 9 pressure units per unit time and greater than or faster than a pressure increase whose rate is 5 pressure units per unit time.

At block 134 the controller compares the rate of pressure change in the head zone to at least one head end rate limit, and compares the rate of pressure change in the foot zone to at least one foot end rate limit, which need not have the same magnitude as the head end rate limit, to determine if the rates are consistent with an occupant having migrated longitudinally along the mattress, particularly toward the foot end of the bed. A fast rate of change may suggest nothing more than an occupant having sat up or otherwise acted in a purposeful way to change his location and/or weight distribution on the bed. A slower rate of change may be consistent with the occupant having migrated along the bed. A very slow rate may not suggest anything conclusive and therefore, by default, would be considered inconsistent with occupant migration. An inference can then be made, in response to the comparing steps, whether or not occupant migration has occurred. If the rate comparison suggests that the occupant has migrated along the bed the test is considered to be positive for occupant migration. If the rate comparison suggests that the occupant has not migrated along the bed the test is considered to be negative for occupant migration. Typically the rate comparison will compare the established actual rate of pressure change to an upper rate limit (suggestive of deliberate occupant movement) and will yield a positive result if the rate being tested is slower than the upper rate limit. Alternatively the rate comparison will yield a positive result if the established rate falls within a given range, i.e. if the established rate is slower than an upper rate limit and faster than a lower rate limit. As an example, considering the single head bladder/single foot bladder architecture of FIG. 2, a depressurization of the head bladder that occurs quickly enough to indicate a rapid rate of occupant movement (for example an intentional movement of the occupant such as sitting up) would not suggest occupant migration, whereas a slower depressurization could suggest occupant migration. If it is desired to test the established rate against a range rather than against a single bound, the rate could also be tested against a lower limit so that a depressurization rate slower than the lower limit also would not suggest occupant migration. Similarly, a pressurization of the foot bladder that occurs quickly enough to indicate a rapid rate of occupant movement would not suggest occupant migration, whereas a slower pressurization could suggest occupant migration. If it is desired to test the established foot end rate against a range rather than against a single limit, the established rate could also be tested against a lower limit so that pressurization rate slower than the lower limit would not suggest occupant migration. Yet another example is the combination of a depressurization rate in the head zone and a pressurization rate in the foot zone, both of which rates are slow enough to suggest occupant migration or fall within a range suggestive of occupant migration. It is believed that the combination test is superior to either of the tests involving only the head zone or the foot zone.

Similar tests of the rate of change of bladder pressure in comparison to one or two limits can be carried out with a mattress architecture having multiple bladders in the head and/or foot zones, such as those of FIGS. 3-6. In such cases the rate test for a given zone (head or foot) will be considered positive if it is positive for any bladder in that zone.

Figure 9:
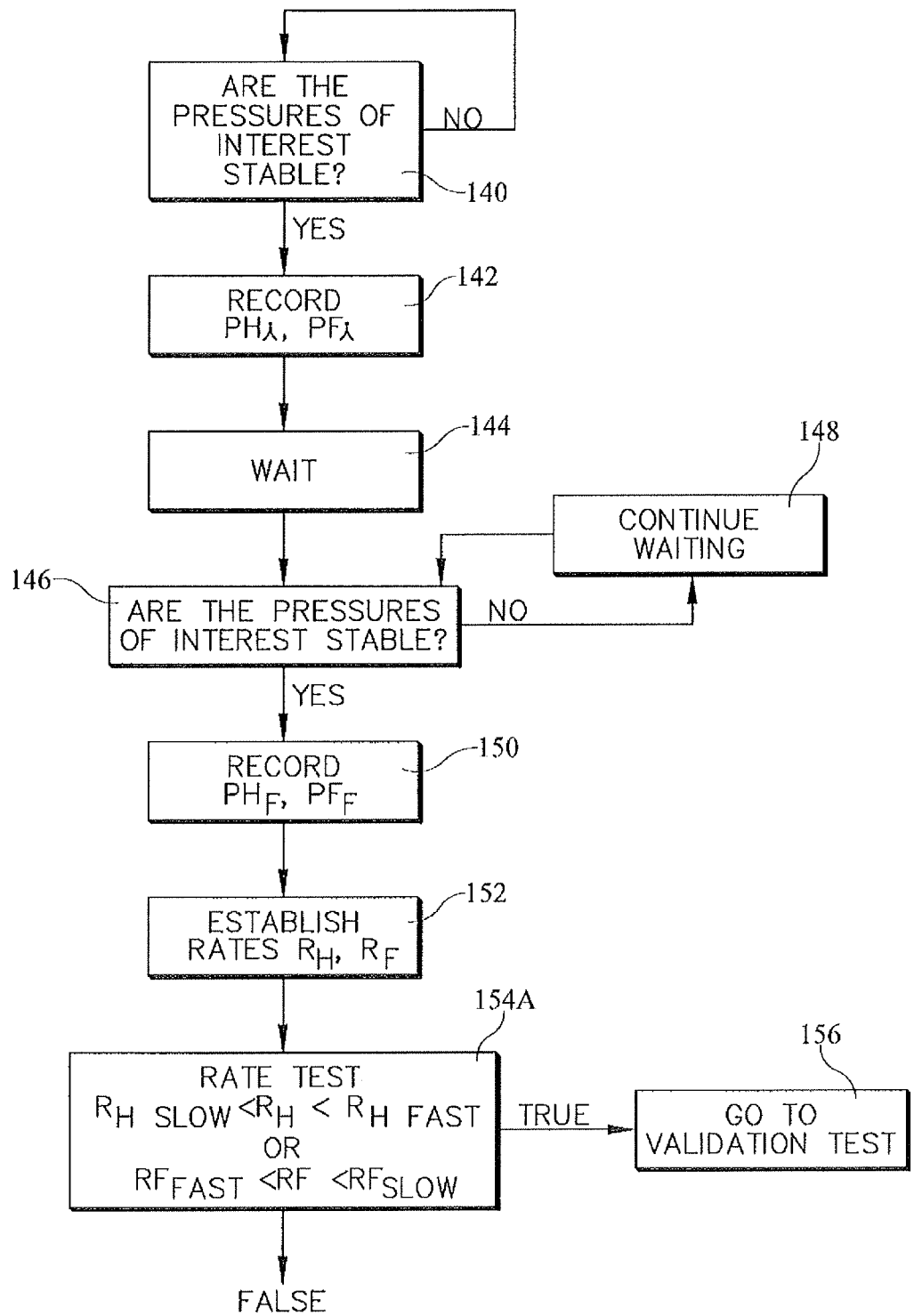
FIGS. 9-10 are a block diagrams showing more detailed versions of the general method of FIG. 7.

FIG. 9 shows a specific variant of the general method. The method begins at block 140 with an assessment of the stability of the pressures of interest as already described. If the pressures of interest are stable the method proceeds to block 142 where an initial head zone pressure $PH_i$ and an initial foot zone pressure $PF_i$ are recorded. At block 144 the method waits for a period of time equal to $t_w$ and then proceeds to block 146 to reassess the stability of the pressures of interest. If the pressures aren't stable the method proceeds to block 148 and continues to wait one or more additional time intervals. When the pressures have stabilized the method advances to block 150 where the "final" pressures $PH_f$ and $PF_f$ are recorded. The method then proceeds to block 152 where the pressure change rates are established. At block 154A a rate test is conducted. The illustrated rate test compares the rate RH of pressure change in the head bladder to lower and upper limits $RH_{slow}$ and $R_{Hfast}$. The illustrated rate test also compares the rate RF of pressure change in the foot bladder to lower and upper limits $RF_{slow}$ and $RF_{fast}$. The illustrated test is a "weak" test in that it employs a Boolean OR to infer that the occupant has migrated along the bed. That is, the occupant is inferred to have migrated along the bed provided that either the head zone pressure has changed at a rate bounded by upper and lower limits or the foot zone pressure has changed at a rate bounded by upper and lower limits.

If the outcome of the rate test is TRUE, the inference of occupant migration can be accepted as conclusive. Alternatively, if the outcome of the rate test is TRUE the inference of occupant migration may be followed by a validation step shown at block 156 and described below in more detail.

Figure 10:
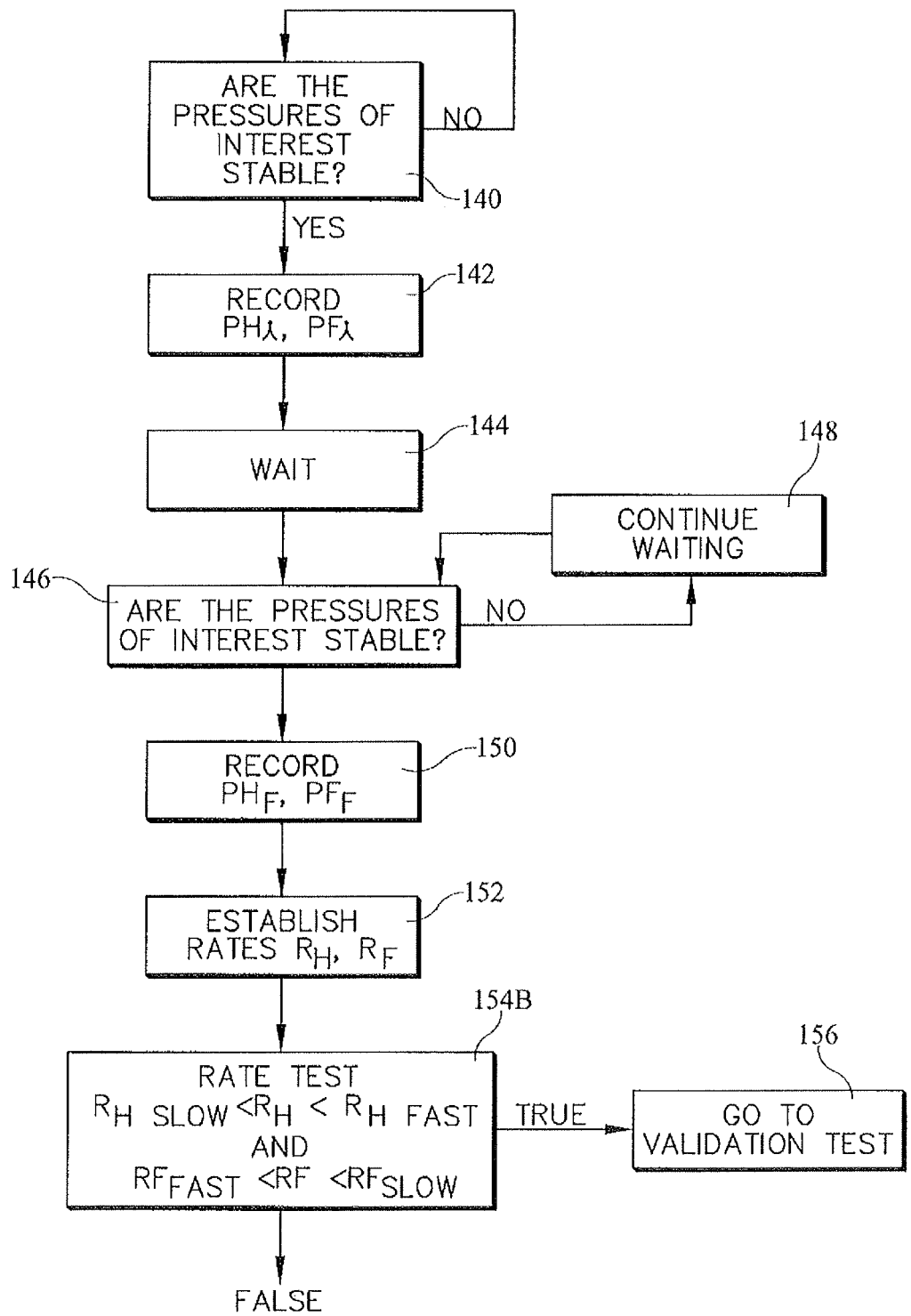

FIG. 10 shows a variant of the method similar to that of FIG. 9 except that it uses a Boolean AND to conduct a "strong" test at block 154B so that the occupant is inferred to have migrated along the bed only if both the head zone pressure and the foot zone pressure have changed at a rate bounded by upper and lower limits.

Figure 11A:
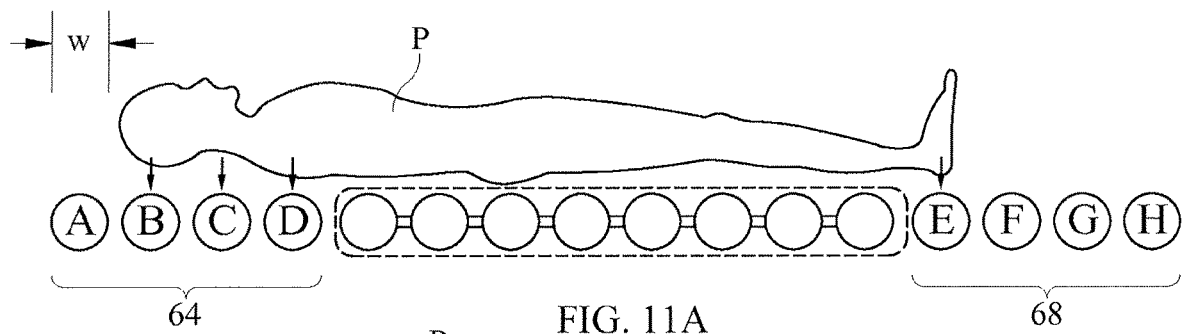
FIGS. 11A-11C are a sequence of views showing a bed occupant migrating footwardly on a bed having multiple bladders in both the head and foot zones.
Figure 11B:
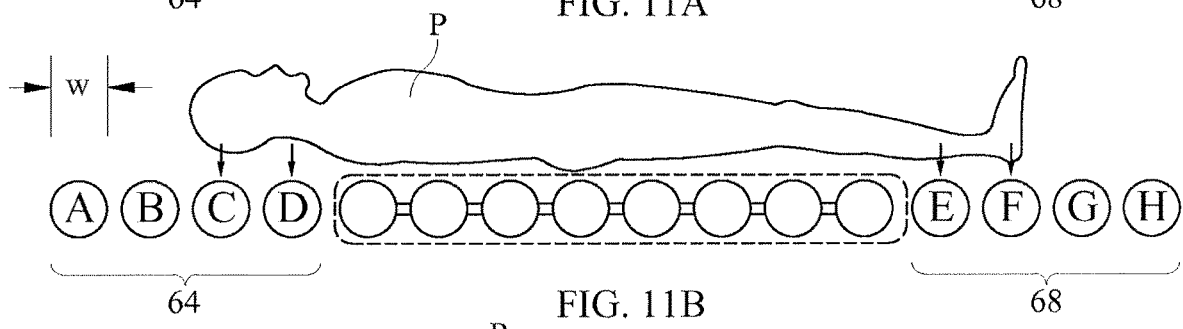
Figure 11C:
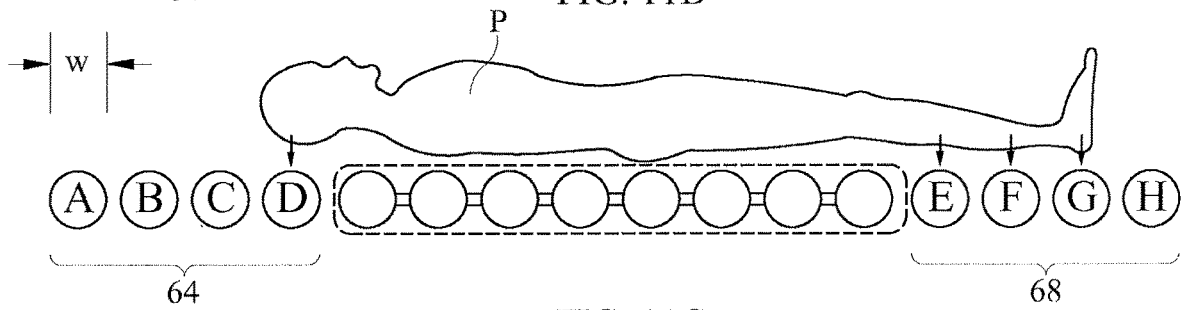
Figure 11D:
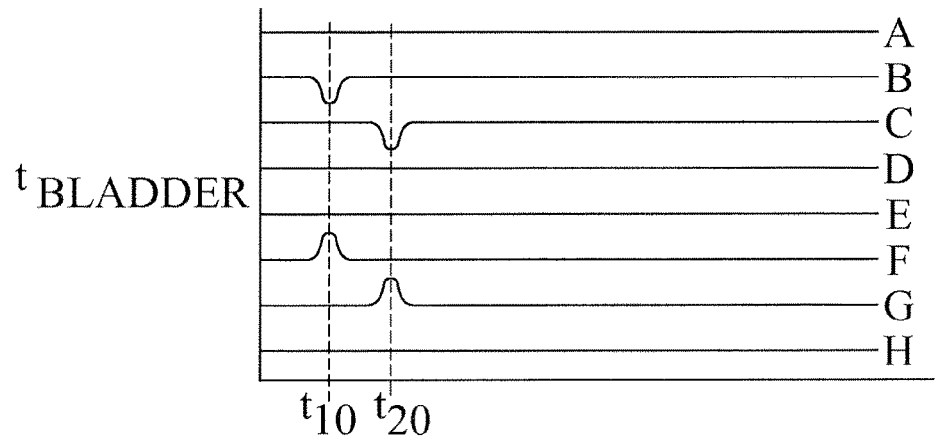
FIG. 11D is a graph of bladder pressure versus time illustrating the method used in conjunction with the bed having multiple bladders in both the head and foot zones.

FIGS. 11A-11D illustrate the method used in conjunction with a bed having multiple bladders in both the head and foot zones. The bed occupant P is initially located over head bladders B, C, and D and over foot bladder E (FIG. 11A). At a later time $t_{10}$ the occupant has migrated footwardly and is located over head bladders C and D and over foot bladders E and F (FIG. 11B). Referring to FIG. 11D, during migration the occupant's weight shifts off bladder B causing the pressure in bladder B to decrease to its lower limit, at which time controller 110 commands operation of blower 100 and valves 104 to repressurize the bladder to its set point pressure. During migration the occupant's weight also shifts onto bladder F causing the pressure in bladder F to increase to its upper limit, at which time controller 110 commands operation of blower 100 and valves 104 to relieve the pressure in the bladder to its set point pressure. As discussed previously the rate of pressure decay in head zone bladder B in comparison to a rate limit, and/or the rate of pressure rise in foot zone bladder F in comparison to a rate limit results in an inference that the occupant has migrated footwardly. At a still later time $t_{20}$ the occupant has migrated footwardly a further amount and is located over head bladder D and over foot bladders E, F, and G (FIG. 11C). During migration the occupant's weight shifts off bladder C causing the pressure in bladder C to decrease to its lower limit, at which time controller 110 commands operation of blower 100 and valves 104 to repressurize the bladder to its set point pressure. During migration the occupant's weight also shifts onto bladder G causing the pressure in bladder G to increase to its upper limit, at which time controller 110 commands operation of a blower 100 and valves 104 to relieve the pressure in the bladder to its set point pressure. The rate of pressure decay in head zone bladder C in comparison to a rate limit, and/or the rate of pressure rise in foot zone bladder G in comparison to a rate limit results in an inference that the occupant has migrated further footwardly. Thus, the use of multiple bladders can not only allow an inference that the occupant has migrated along the mattress, but can also offer progressively changing information about the actual location of the occupant. As already noted the quantity of test bladders depends on the degree of granularity considered to be acceptable.

Referring back to FIGS. 9-10, when the method is applied to architectures with multiple bladders in the head and/or foot zones (such as FIGS. 12A-12C) the method would carry out the stability tests (blocks 140, 146) recording step (blocks 142, 150) and establishment step (block 152) for each of the test bladders in the zone. The rate test step of block 154A or 154B would also be carried out for each bladder. The result of the rate test would be TRUE if the pressure change rate in any one of the head zone bladders were less than the upper limit for that zone. Alternatively the result of the rate test would be TRUE if the pressure change rate in any one of the foot zone bladders were less than the upper limit for that zone. In yet another alternative the result of the rate test would be TRUE if the pressure change rate in any one of the head zone bladders or in any one of the foot zone bladders were within upper and lower limits for that zone (i.e. the "weak" test described above). In yet another alternative the result of the rate test would be TRUE if the pressure change rate in any one of the head zone bladders and in any one of the foot zone bladders were within upper and lower limits for that zone (i.e. the "strong" test described above).

For the architectures that use multiple bladders in the head and seat zones the upper and lower rate limits can be the same from bladder to bladder within each zone, in which case the rate limits for all the head zone bladders may or may not be the same as the rate limits for all the foot zone bladders. Alternatively, the rate limits could differ from bladder to bladder. Differing rate limits could improve accuracy by accounting for the weight imposed on the mattress by different parts of an occupant's body (e.g. head, neck, shoulders/upper back, lower back, buttocks, thighs, popliteal region, calves and heels). Bladder specific limits could be associated with individual bladders by way of a user interface 116 and may be based on factors such as occupant height and/or morphology. Moreover, controller 110 can be programmed to reassociate the bladder specific limits from one bladder to the next in response to perceived occupant migration.

Figure 12:
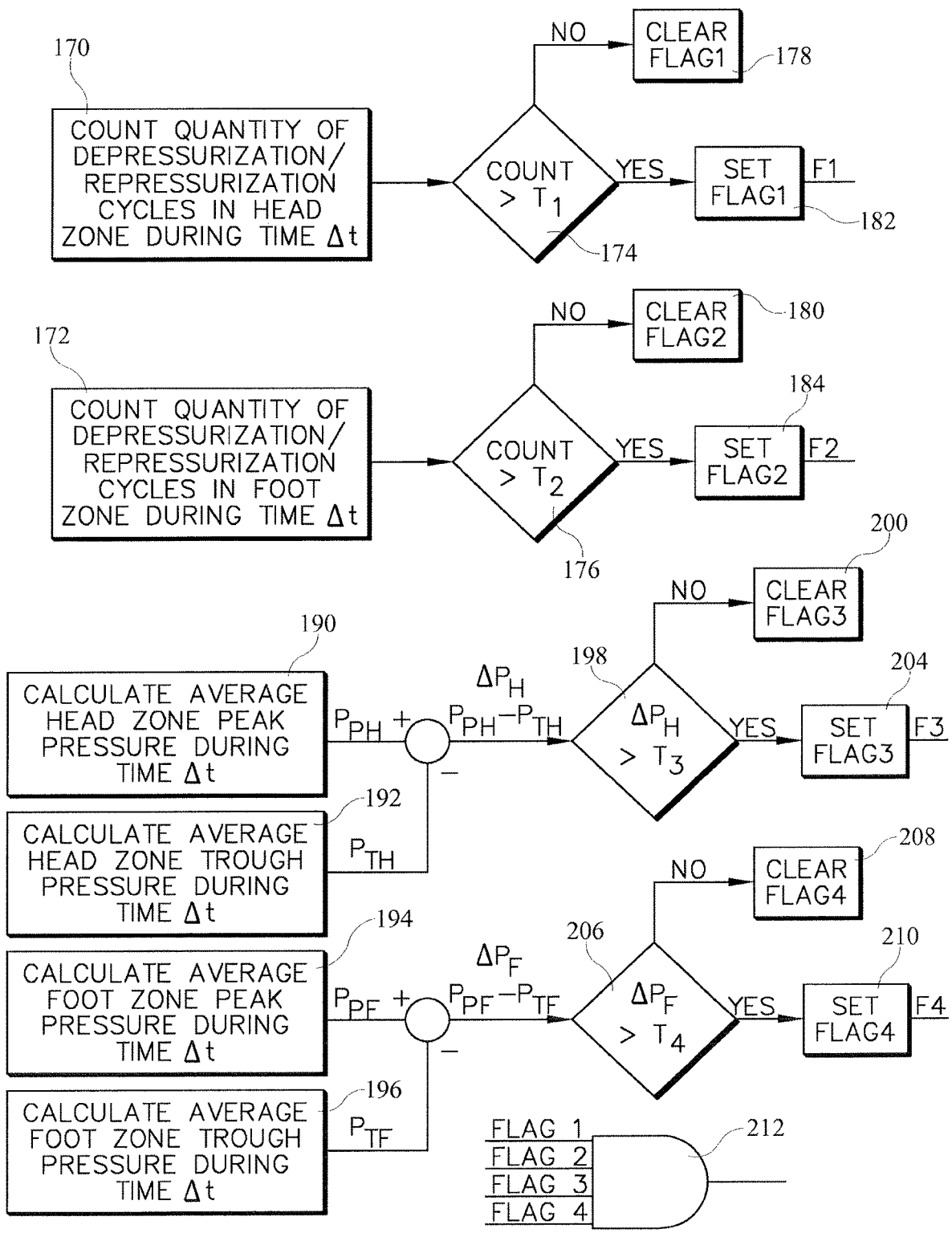
FIGS. 12-14 are a block diagram and pressure vs. time graphs for another method of detecting a change in occupant location.
Figure 13:
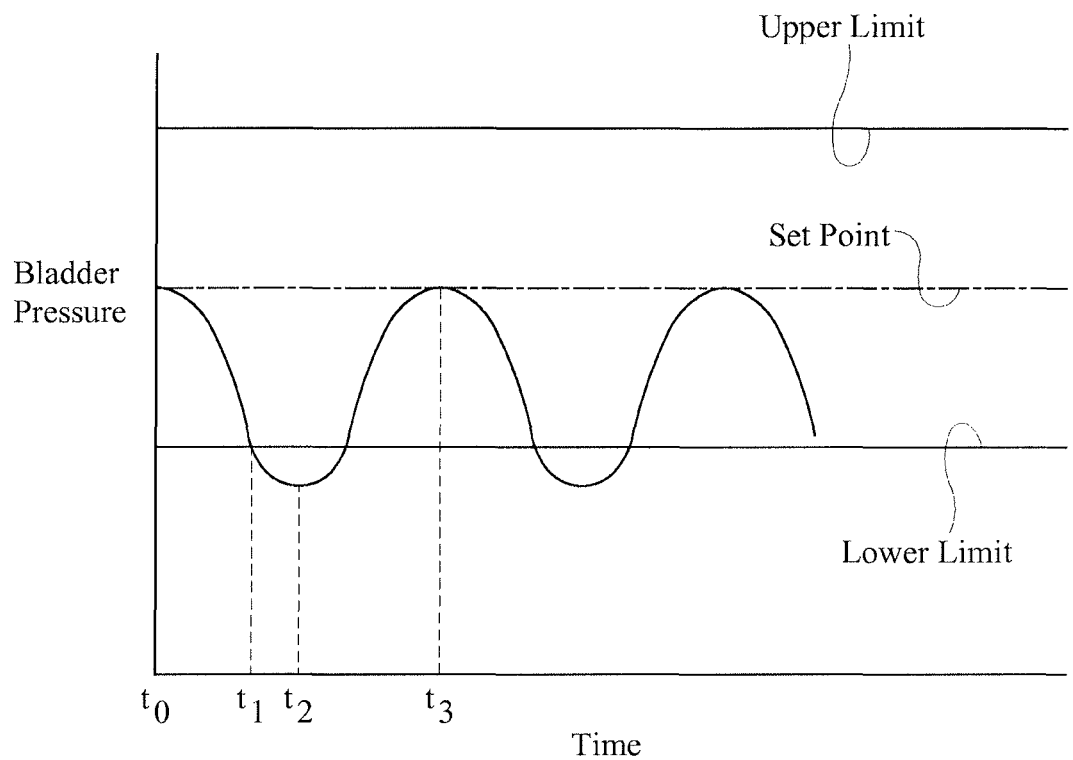
Figure 14:
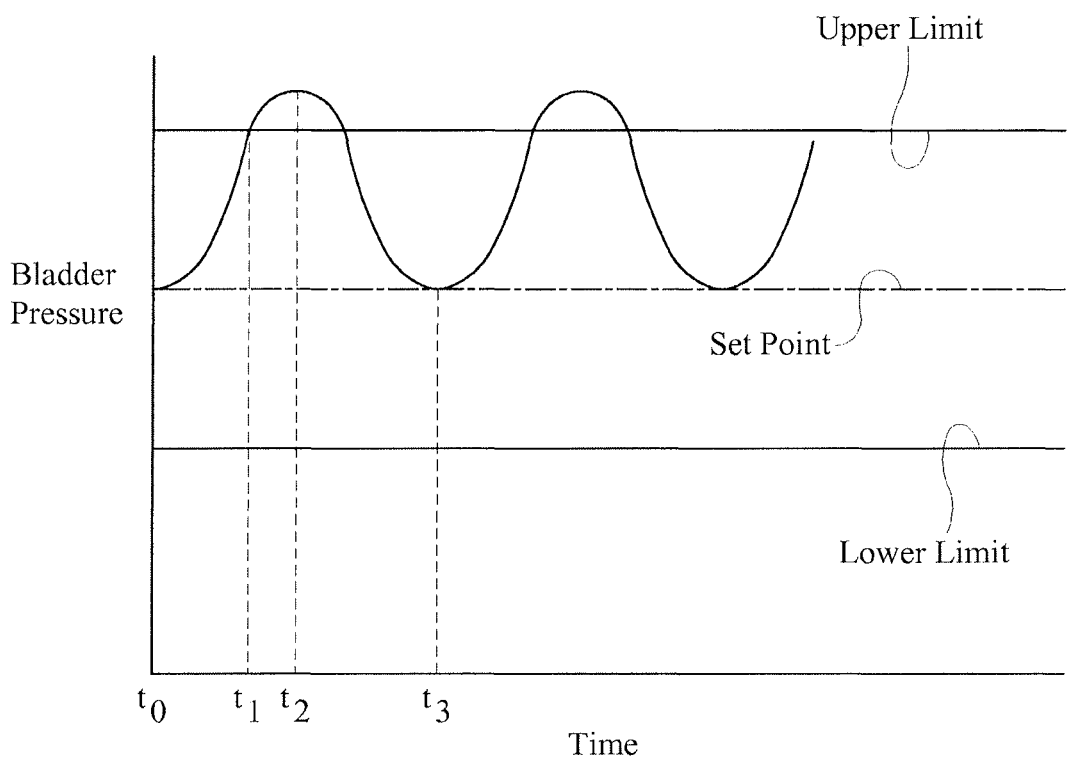

FIGS. 12-14 show a block diagram and pressure vs. time graphs for another method of detecting a change in occupant location. As in the previously described method, the method of FIGS. 12-14 assumes that that the rate of pressure decrease in the head end bladder and the rate of pressure increase in the foot end bladder are slow enough to be consistent with occupant migration rather than with a more abrupt transference of weight. The method further assumes that the changes in bladder pressure during occupant migration are fast enough and that the system dynamics are slow enough that the actual bladder pressures exceed the lower limit for the head bladder and exceed the upper limit for the foot bladder at some time during the occupant migration.

According to the method, as the occupant migrates footwardly on the bed, bladder pressure in the head bladder decreases and bladder pressure of the foot bladder increases in the time interval between t0 and t1. When the head end bladder pressure falls below its lower limit and the foot end bladder pressure rises above its upper limit the controller commands operation of the blower and valves appropriate for restoring bladder pressures to the set point pressures. At time t2 the bladder pressures begin to respond. At time t3 the bladder pressures have returned to their set point values. As the occupant continues to migrate footwardly, his weight is transferred progressively off the head zone and onto the foot zone. Accordingly, bladder pressures in those zones undergo additional cycles of change between peak and trough values. At block 170 the method counts the number of pressurization and depressurization cycles that have occurred in the head zone during a time interval Δt. At block 172 the method counts the number of pressurization and depressurization cycles that have occurred in the foot zone during the same time interval Δt. For the head zone the peak pressure is shown as approximately the pressure midway between the lower and upper limits, and the trough pressure is a pressure lower than the lower limit. At blocks 174, 178, 182 a first flag F1 is set if the number of pressure change cycles per unit time in the head zone exceeds a first count threshold T1. At blocks 176, 180, 184 a second flag F2 is set if the number of pressure change cycles per unit time in the foot zone exceeds a second count threshold T2. Block 190 calculates the average peak pressure $P_{PH}$ in the head zone during the time interval under consideration. Block 192 calculates the average trough pressure $P_{TH}$ in the head zone during the same time interval. Blocks 194 and 196 calculate similar time averaged peak and trough pressures $P_{PF}$, $P_{TF}$ in the foot zone bladders. The method determines ΔPH, the difference between the time average peak and trough pressures in the head zone. At blocks 198, 200, 204 the method determines if that difference of time averaged pressures exceeds a pressure difference threshold T3. If so, the method sets a third flag F3. The method also determines ΔPF, the difference between the time average peak and trough pressures in the foot zone. At blocks 206, 208, 210 the method determines if that difference of time averaged pressures exceeds a pressure difference threshold T4. If so, the method sets a fourth flag F4. As indicated by AND gate 212 the method tests whether all four flags have been set (i.e. all four flags have a TRUE value). If so, the test produces a TRUE result thereby inferring that the occupant has migrated longitudinally along the bed.

In the example of FIGS. 12-14 the pressure cycles are depicted as having approximately equal amplitudes and periods and are shown as being 180 degrees out of phase. However in practice the amplitudes and periods may be unequal and the phase difference, if any, may be other than 180 degrees.

If the mattress head zone or foot zone has only a single bladder as in FIG. 2, the above described method would rely on the pressure cycle counts and the pressure differences associated with the single head and foot bladder. Referring to FIG. 15 if the mattress head or foot zone has multiple bladders (as in FIGS. 3-6) the test for cycle count would be considered TRUE for the head zone if that test were TRUE for any one of the bladders in the head zone, and the pressure difference test would be considered TRUE for the head zone if that test were TRUE for any one of the bladders in the head zone. Similarly, the test for cycle count would be considered TRUE for the foot zone if that test were TRUE for any one of the bladders in the foot zone, and the pressure difference test would be considered TRUE for the foot zone if that test were TRUE for any one of the bladders in the foot zone. As seen in FIG. 15 the cycle count test and the pressure difference test need not be TRUE for the same bladder in the head zone. Likewise the cycle count test and the pressure difference test need not be TRUE for the same bladder in the foot zone. However imposing the criterion that both the cycle count test and the pressure difference test must be TRUE for the same bladder may be beneficial. Moreover, it may be beneficial to require that the cycle count test and the pressure difference test yield a TRUE result for corresponding bladders in the head zone and in the foot zone. A head zone bladder and a foot zone bladder are corresponding bladders if their relative responses to occupant migration (e.g. the outcome of the cycle count test, the pressure difference or some other suitable test) are correlatable. One simple example is a foot end bladder that can be expected to become more heavily loaded and a head end bladder that can be expected to become more lightly loaded approximately concurrently with the head end bladder becoming more heavily loaded as an occupant migrates longitudinally along the mattress.

In each of the above described methods the inference drawn from the changes in bladder pressure during an interval of time may be accepted as conclusive. Alternatively, a validation test can be conducted as seen at block 156 of FIGS. 9-10. One example test is referred to as a dynamic or active test because it involves making an intentional change in bladder pressure. This differs from the tests already described which can be considered to be passive tests because they do not involve making an intentional change in bladder pressure.

Figure 16:
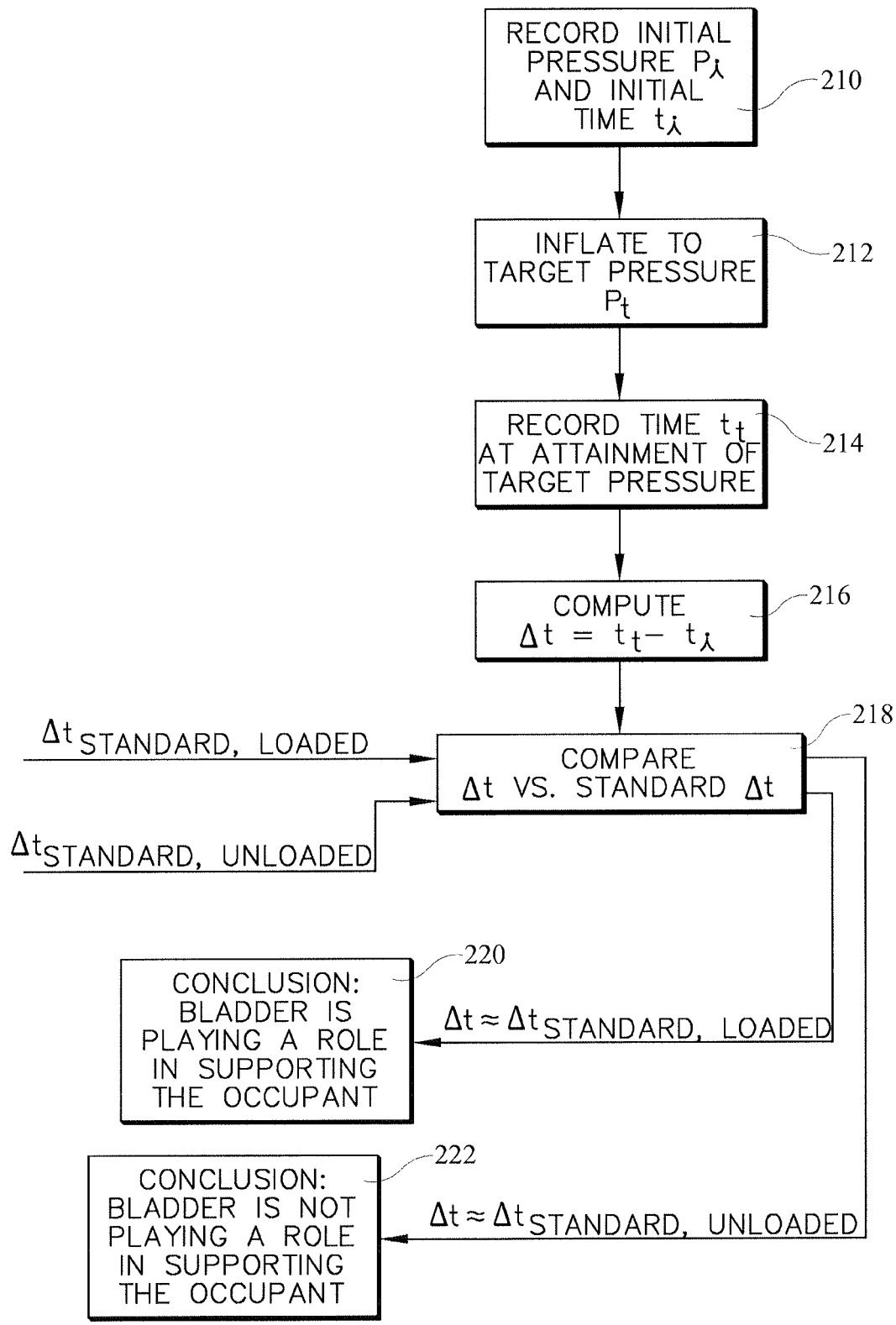
FIG. 16 is a block diagram illustrating a validation test.

FIG. 16 shows one embodiment of an active test in which at least one test bladder in the head zone and one in the foot zone are pressurized from an initial pressure $P_i$ to a specified target pressure $P_t$. Block 210 records the initial pressure $P_i$ and the time $t_1$ at which the pressure reading is taken. The pressurization occurs at block 212. At block 214 the method records the time at which the target pressure $P_t$ is achieved. At block 216 the elapsed time for pressurization is determined. A bladder that is not involved in supporting an occupant will achieve the target pressure more quickly than a bladder that is involved in supporting the occupant. Hence, block 218 compares the pressurization times to standard times required for pressurization, plus or minus a tolerance, which gives an indication of whether the bladder in question is loaded (playing a role in supporting the occupant—block 220) or unloaded (not playing a role in supporting the occupant—block 222). By comparing the pressurization times to the standard pressurization times that would be expected for a properly positioned occupant, an assessment can be made of the occupant's position on the mattress and whether that position is satisfactory or is consistent with a migrated occupant. If desired the standard pressurization times can be correlated with particular segments of an occupant's body. For example an occupant's head and shoulders might apply more weight on the bladders than the occupant's neck, and the occupant's shoulders might apply more weight than that occupant's head. Accordingly, a group of bladders that exhibits, a moderate pressurization rate, a faster pressurization rate, and a slow pressurization rate slower than the moderate rate can be used to assess the occupant's position on the mattress.

Other ways of analyzing the dynamics of bladder pressurization are also contemplated. For example in a mattress with a multi-bladdered test zone, rather than comparing pressurization times to standard times, one could compare the relative pressurization times of the bladders to each other. Bladders exhibiting pressurization times that differ by at least a threshold amount, would provide information about the occupant's location on the mattress, particularly if those bladders are adjacent to each other in the same zone and/or the identity of the loaded and unloaded bladders in each zone is consistent with a possible occupant position, satisfactory or otherwise. For example referring again to FIG. 11A-11B, assume that the occupant initially occupied four test bladders, three in the head test zone (bladders B, C, D) and one (bladder E) in the foot test zone (FIG. 11A) and that a passive test resulted in an inference that the occupant had, over time, migrated footwardly by one bladder width W (FIG. 11B). If the active test reveals that the occupant still occupies four bladders and that the identity of those bladders is bladders C, D in the head test zone and E, F in the foot test zone, then the active test validates the inference from the passive test that the occupant has migrated one bladder width toward the foot end of the bed.

If the test zone comprises multiple bladders the bladders can be pressurized for the active test concurrently, nonconcurrently in groups, or nonconcurrently individually.

An alternative to an active test based on bladder pressurization time is to vent the bladder and determine the time required for depressurization. Bladders involved in supporting the occupant will depressurize more quickly than those not involved in supporting the occupant If the dynamic test is carried out on the basis of bladder pressurization, the test results may benefit from a preliminary step of depressurizing the test bladder prior to pressurizing it. The test results may also benefit from a preliminary step of depressurizing one or more bladders on or both sides of the test bladder.

If the dynamic test is carried out on the basis of bladder depressurization, the test results may benefit from a preliminary step of overpressurizing the test bladder prior to depressurizing it. The test results may also benefit from a preliminary step of depressurizing one or more bladders on either side of the test bladder instead of or in addition to overpressurizing the test bladder.

If patient migration is determined to have occurred, one or more actions can be taken. Examples include issuing an alarm, taking an action intended to mitigate additional migration such as placing the deck in a head down orientation, and taking an action to mitigate any adverse effects of the migration such as the shear and tissue stretch mitigation technique described in pending U.S. patent application Ser. No. 12/704,600 entitled "Method and Apparatus for Relieving Shear Induced by an Occupant Support", the contents of which are incorporated herein by reference. Another technique that may be required is to elevate the pressure in any bladder that is perceived to have been subjected to a higher load (i.e. occupant weight) than that particular bladder would have otherwise been expected to bear based on normal occupant weight distribution.

The foregoing disclosure contemplates that controller 110 will carry out an algorithm corresponding to one of the passive tests by default. Alternatively, the controller could be set up so that operation of the algorithm is selectable and deselectable by a user input to user interface 116. In either case, the algorithm's progress is suppressed if the bed (frame or mattress) is adjusted in any way that is predicted to cause the bladder pressures to change in such a way as to mimic the changes associated with occupant migration. In the limit, one might unconditionally suppress the test for any adjustment to the bed rather than try to predict which adjustments might cause a false positive for occupant migration. Example adjustments include changing the angular orientation of a deck section or inflating a turn assist bladder. Alternatively, one could delay the onset of the commanded adjustment until the test progressed to a point where the adjustment wouldn't affect the test. However it is believed this may be less satisfactory to the occupant and/or caregiver, and would also have to exempt time critical adjustments, such as adjusting the bed to a condition suitable for CPR.

Although this disclosure refers to specific embodiments, it will be understood by those skilled in the art that various changes in form and detail may be made without departing from the subject matter set forth in the accompanying claims.

The invention claimed is:

1. A bed comprising:
a frame;
a mattress supported by the frame, the mattress including a head zone having at least one fluid pressurizable bladder and a foot zone having at least one fluid pressurizable bladder;
a controller operable to:
compare a head end rate of pressure change to at least one head end rate limit;
compare a foot end rate of pressure change to at least one foot end rate limit; and
infer, in response to the comparing steps, whether or not occupant migration has occurred.

2. The bed of claim 1 in which the head zone and the foot zone each include multiple bladders.

3. The bed of claim 1 in which the head zone and the foot zone are longitudinally separated from each other by an intermediate zone.

4. The bed of claim 3 in which one or more bladders resides in the intermediate zone, the bladders being the principal medium for supporting an occupant of the mattress in the intermediate zone.

5. The bed of claim 3 in which a medium other than one or more bladders resides in the intermediate zone and is the principal medium for supporting an occupant of the mattress in the intermediate zone.

6. The bed of claim 5 in which the medium is foam.

7. The bed of claim 2 in which the head zone, the foot zone or both include a foam medium for at least partially supporting an occupant of the bed, the foam medium having a frame side and an occupant side, and in which the at least one head zone bladder is embedded in the foam medium.

8. The bed of claim 2 in which the head zone, the foot zone or both include a foam medium for at least partially supporting an occupant of the bed, the foam medium having a frame side and an occupant side, and in which the at least one head zone bladder is exposed on the frame side of the medium.

9. The bed of claim 2 in which the head zone, the foot zone or both include a foam medium for at least partially supporting an occupant of the bed, the foam medium having a frame side and an occupant side, and in which the at least one head zone bladder is exposed on the occupant side of the medium.

10. The bed of claim 1 in which the at least one head end rate limit is a fast head end rate limit, and the at least one foot end rate limit is a fast foot end rate limit.

11. The bed of claim 10 in which the inference is a positive result for occupant migration if the head end pressure rate is slower than the fast head end rate limit or if the foot end pressure rate is slower than the fast foot end rate limit.

12. The bed of claim 10 in which the inference produces a positive result for occupant migration if the head end pressure rate is slower than the fast head end rate limit and if the foot end pressure rate is slower than the fast foot end rate limit.

13. The bed of claim 10 including a slow head end rate limit and a slow foot end rate limit.

14. The bed of claim 13 in which the inference is a positive result for occupant migration if the established head end pressure rate is slower than the fast head end rate limit and faster than the slow head end rate limit or if the established foot end pressure rate is slower than the fast foot end rate limit and faster than the slow foot end rate limit.

15. The bed of claim 13 in which the inference is a positive result for occupant migration if the established head end pressure rate is slower than the fast head end rate limit and faster than the slow head end rate limit and if the established foot end pressure rate is slower than the fast foot end rate limit and faster than the slow foot end rate limit.

16. The bed of claim 1 in which the inference produces a result with regard to occupant migration and the result is accepted as conclusive.

17. The bed of claim 1 in which when the inference is a positive result for occupant migration, the inferring step is followed by a validation.

18. The bed of claim 17 in which the validation includes
changing at least one of pressure in the head zone and pressure in the foot zone in response to the inferred positive result;
determining a head end pressure derivative based on the change in pressure in the head zone and/or determining a foot end pressure derivative based on the change in the pressure in the foot zone;
conducting a comparison of the pressure derivative or derivatives and an associated pressure derivative threshold; and concluding, in response to the conducting step, whether or not occupant migration has occurred.

19. The bed of claim 18 in which:

both the pressure in the head zone and the pressure in the foot zone are changed in response to the inferred positive result;

the determining analysis is carried out for both the head zone and the foot zone; and the concluding analysis is positive for occupant migration if the comparison for the head zone, the comparison for the foot zone, or both indicate occupant migration.

20. The bed of claim 16 in which the conclusion of occupant migration is followed by the controller doing any one of:

issuing an alarm;

taking an action intended to mitigate additional migration; and taking an action to mitigate adverse effects of the migration.

* * * * *